United States Patent [19]

Bittner

[11] Patent Number: 4,536,896
[45] Date of Patent: Aug. 27, 1985

[54] INTRAOCULAR LENS WITH APPENDAGE MANIPULATION LOOP

[75] Inventor: Timothy Bittner, Duarte, Calif.

[73] Assignee: Ioptex Inc., Azusa, Calif.

[21] Appl. No.: 495,415

[22] Filed: May 17, 1983

[51] Int. Cl.³ .......................... A61F 1/16; A61F 1/24
[52] U.S. Cl. ........................................................ 623/6
[58] Field of Search .......................................... 3/13, 1

[56] References Cited

U.S. PATENT DOCUMENTS

| | | | |
|---|---|---|---|
| 4,343,050 | 8/1982 | Kelman | 3/13 |
| 4,363,143 | 12/1982 | Callahan | 3/13 |
| 4,446,581 | 5/1984 | Blake | 3/13 |

OTHER PUBLICATIONS

Intermedics Intraocular Lenses, Intermedics Intraocular Inc., P.O. Box 70670, Pasadena, Calif. 91107 (advertisement) Apr. 1982, Model 045.
Lens Styles from Cilco, advertisement brochure, Oct. 1982, S-Flex Anterior Chamber Lens and Kelman Quadraflex Anterior Chamber Lens.

Primary Examiner—Ronald L. Frinks
Attorney, Agent, or Firm—Bielen & Peterson

[57] ABSTRACT

An intraocular lens utilizing an optical portion and having at least one appendage connected to the same at the first end portion. The appendage includes a second end portion which is intended for contacting the anatomy of the eye. The appendage also includes an intermediate portion between the first and second end portions which is provided with a substantially closed loop to aid in manipulation of the appendage.

5 Claims, 5 Drawing Figures

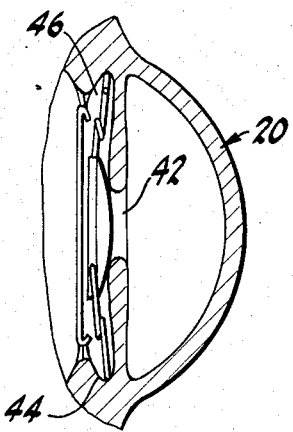
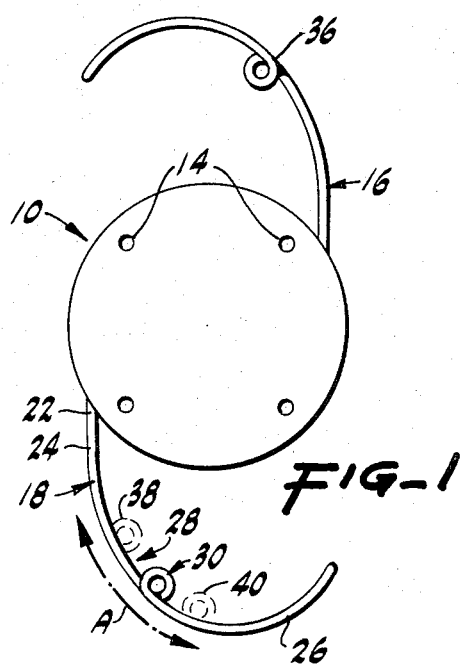
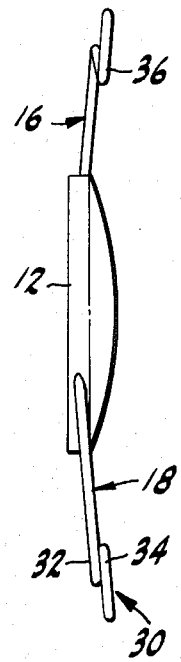
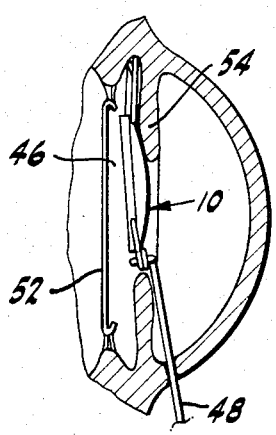
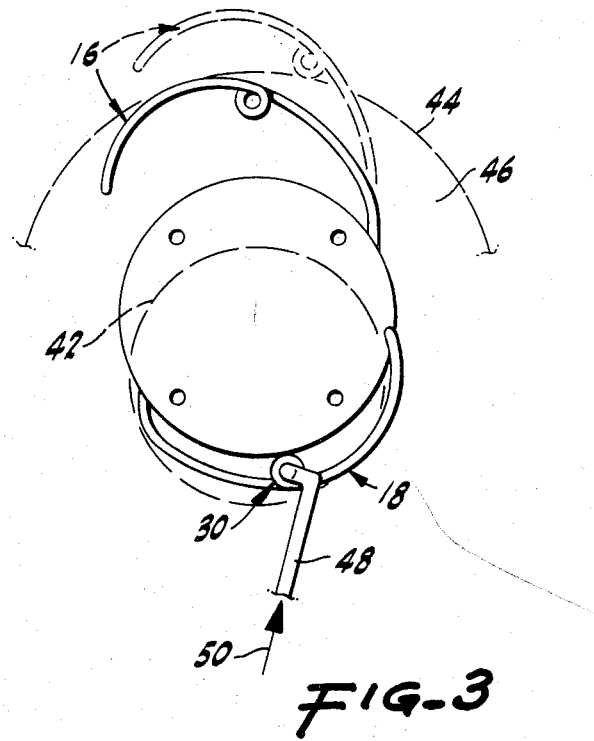

INTRAOCULAR LENS WITH APPENDAGE MANIPULATION LOOP

BACKGROUND OF THE INVENTION

The present invention relates to a novel and useful intraocular lens which includes a mechanism for manipulation of the appendages which support the intraocular lens within the eye.

Intraocular lenses are placed within the eye after cataract surgery to replace the optical function of the natural lens which have been removed in whole or in part. Many intraocular lens designs include an optical portion and one or more appendages which extend therefrom and are used to engage the peripheral portions of the eye in either the anterior of posterior chamber. For example reference is made to the U.S. Pat. No. 4,159,546 to Shearing which shows a typical intraocular lens having two open loops curving in opposite directions. To place the lens depicted in this reference within the posterior chamber would require first passing the inferior loop of lens through the pupil and into the posterior chamber. The superior loop is then grasped with a pair of forceps and compressed or bent against the optical portion and pushed into the posterior in this position. Once the superior loop is in the posterior chamber it would be released causing the appendage of the intraocular lens to spring into place. The lens is then rotated as desired by the surgeon.

It is often a very difficult procedure for the surgeon to grasp the superior loop and compress the same against the optical portion of the lens. Placing a notch in the appendage would only provide a position which is employed to push the appendage. This restricts the maneuverability of the lens as it is being implanted.

An intraocular lens which provides an improved manipulation of the appendages used for fixation of the same would be a great advance in the medical field.

SUMMARY OF THE INVENTION

In accordance with the present invention a novel intraocular lens having appendage with a manipulation loop for facilitating implantation is provided.

The intraocular lens of the present invention has an optical portion which may be of conventional design. Connected to the optical is at least one appendage having a first end portion connected to and extending from the optical portion. The appendage also includes a second end portion intended for contacting the anatomy of the eye and thus holding the intraocular lens in place. Finally the appendage includes an intermediate portion between the first and second end portions which includes a closed loop. Loop may be used for the insertion of a tool which would permit the easy compression of the appendage against the optical portion and the movement of the entire lens in many directions.

The substantially closed loop of the intermediate portion of the appendage may be formed from a continuous member which curves through an arc of greater than one hundred and eighty degrees. For example the continuous curved elongated member may be formed as a coil having an upper portion and adjacent lower portion provided with an overlapped area. In many cases the substantially closed loop could be located at about the mid point between place of end connection of said first end portion to the optical portion and the end of the second end portion.

The intraocular lens having such a loop may be manufactured by connecting an appendage previously described to an optical portion. A substantially closed loop may then be formed in the intermediate portion by turning the appendage a distance greater than one hundred and eighty degrees and fixing the loop in that position. For example the turning of the loop may be accomplished at room temperature. Subsequent heating and cooling of the formed loop maintains the loop in the desired configuration.

It may be apparent that a novel and useful intraocular has been described.

It is therefore an object of the present invention to provide an intraocular lens having an appendage manipulation loop which facilitates the insertion of the intraocular lens after cataract removal.

Is another object of the present invention to provide an intraocular lens which includes a manipulation mechanism which permits the user to move the intraocular lens in many directions without the use of a forcep tool.

It is yet another object of the present invention to provide an intraocular lens having an appendage manipulation loop which permits the user to collapse the appendage of the intraocular lens against the optical portion to aid in the pushing of the intraocular lens through the pupil and into the posterior chamber of the eye during the implantation period.

Still another object of the present invention is to provide an introcular lens having an appendage manipulation loop which may be quickly and easily manufactured using conventional materials.

The invention possesses other objects and advantages especially as concerns particular characteristics and features thereof which will become apparent as the specification continues.

BRIEF DESCRIPTION OF THE DRAWINGS

FIG. 1 is a top plan view of the intraocular lens of the present invention.

FIG. 2 is a side view of the intraocular lens of the present invention.

FIG. 3 is a top plan view of the intraocular lens of the present invention being inserted into the posterior chamber of the eye.

FIG. 4 is a sectional view depicting the insertion maneuver of FIG. 3.

FIG. 5 is a sectional view of an eye showing the lens of the present invention implanted in the posterior chamber of the eye.

For a better understanding of the invention references made to the following detailed description which should be referenced to the hereinabove described drawings.

DESCRIPTION OF THE PREFERRED EMBODIMENTS

Various aspects of the present invention will evolve from the following detailed description of the preferred embodiments thereof which should be taken in conjunction with the hereinabove described drawings.

The invention as a whole is represented in the drawings by reference character 10, FIG. 1. The intraocular lens 10 includes an optical portion 12 which may be constructed of any suitable material such as polymethyl methacrylate, opthalmic glass or the like. A plurality of openings 14 permit the surgeon to move the lens once it is in place as shown in FIG. 5. Lens 10 includes appendages 16 and 18 which may be formed from polypropylene or other known materials.

With references to appendages 16 and 18 following description will concern appendage 18. It should be understood that the same description should apply to appendage 16 or any other like appendages which may be used to fix intraocular lens 10 within eye 20, FIG. 5. Appendage 18 connects to optical portion 12 at end 22 of first end portion 24. Second end portion 26 serves as the distal part of appendage 18 in relation to optical porton 12. Second end portion 26 is intended for contacting the anatomy of the eye which will be described hereinafter. Appendage 18 also includes an intermediate portion 28 which is necessarily located between first and second end portions 24 and 26. Appendage 18 is resilient, a characteristic which may be employed to fix lens 10 within eye 20.

Intermediate portion 28 includes a substantially closed loop 30. With reference to FIG. 2 it may be seen that loop 30 includes a lower portion 32 and an upper portion 34. Loop 30 is a continuous member which curves through an arc of greater than one hundred and eighty degrees. In the embodiment shown in FIG. 1 loop 30 has curved approximately three hundred and sixty degrees such that the curvature of second end portion 26 is essentially a continuation of the curvature of first end portion 24. With reference to FIG. 2 it may be seen that appendages 16 and 18 have an upward camber which is especially useful for placement of lens 10 in the posterior chamber of eye 20. However, lens 10 may be constructed for employment in the anterior chamber of eye 20 if desired. Appendage 16 includes a second closed loop 36 such that appendages 16 and 18 may possess interchangeable functions. Loop 30 may be placed at any point in intermediate portion 28. It has been found that for a loop 8.2 millimeters in length that first end portion 24 may be approximately 3.5 millimeters in length, second end portion 26 may be 1.5 millimeters in length and intermediate porton 28 may be approximately 3.2 millimeters in length. Thus, closed loop 30 may be positioned as shown by phantom circles 38 and 40, FIG. 1.

With reference to FIG. 3 it may be seen that lens 10 is inserted into the eye by placing appendage 16 through enlarged pupil 42 (phantom). Appendage 16 contacts the periphery, ciliary sulcus, 44 in the posterior chamber 46 of eye 20. Appendage 16 is shown moved from its phantom rendition to the solid rendition in that figure. As such, appendage 16 has been chosen as the inferior appendage while appendage 18 is the superior appendage of the intraocular lens 10. The reverse may be the case with the lens type depicted in the drawings. A surgical hook 48 is inserted within loop 30 of appendage 18 to apply pressure along directional arrow 50. With reference to FIG. 4 it may be seen that capsule 52 remains from the cataract removal. Iris 54 has been relaxed to cause the dilation of pupil 42. Further pushing of hook 48 on appendage 18 via loop 30 will cause the superior appendage 18 to enter posterior chamber 46.

Removal of hook 48 from loop 30 will permit appendage 18 to spring into place as shown in FIG. 5. The optical portion 12 and appendage 18 may be inserted without difficulty in one motion. At this point the surgeon may rotate the lens 10 such that appendages 16 and 18 are a substantially horizontal to prevent decentration of the inferior appendage with gravity.

Loop 30 may be easily formed by turning appendage 18 the required angle. A jig or post may be used to aid in this maneuver (not shown). Appendage is then heated to about three hundred sixty degrees in the case of polypropylene and subsequently cooled to fix the formed loop 30 and remaining portions of appendage 18 into the proper orientation.

While in the foregoing embodiments of the present invention have been set forth in considerable detail for the purposes of making a complete disclosure of the invention, it may be apparent to those of skill in the art that numerous changes may be made in such details without departing from the spirit and principles of the invention.

What is claimed is:

1. An intraocular lens comprising:
   a. an optical portion; and
   b. at least one resilient appendage having a first end portion connected to and extending from said optical portion, a second end portion intended for contacting the anatomy of the eye, and an intermediate portion between said first and second end portions, said intermediate portion of said at least one appendage including a substantially closed loop, said substantially closed loop including a continuous member which turns through an arc of at least one hundred eighty degrees, said continuous member forming a coil having an upper portion and an adjacent lower portion provided with an overlapped area, said continuous member of said closed loop being fixed against movement relative to said first end portion of said at least one appendage such that the exertion of force on said at least one appendage results in bending of said first end portion relative to said optical portion.

2. The intraocular lens of claim 1 in which said substantially closed loop is located at substantially the midpoint between said place of connection of said first end portion to said optical portion and the end of said second end portion.

3. The intraocular lens of claim 1 in which said continuous member of said closed loop turns through an arc of at least two hundred seventy degrees.

4. The intraocular lens of claim 1 in which said continuous member of said closed loop turns through an arc of at least three hundred seventy degrees.

5. The intraocular lens of claim 1 in which said closed loop is closer to the optical portion than said second end portion of said at least one appendage in the absence of any bending forces on said at least one appendage.

* * * * *